US009408838B2

(12) United States Patent
Roseman et al.

(10) Patent No.: US 9,408,838 B2
(45) Date of Patent: *Aug. 9, 2016

(54) TREATMENT FOR CEREBRAL PALSY GAIT IMPAIRMENT

(71) Applicant: Gilrose Pharmaceuticals, LLC, White Plains, NY (US)

(72) Inventors: Bruce Roseman, White Plains, NY (US); Gilla Kaplan, New York, NY (US)

(73) Assignee: GILROSE PHARMACEUTICALS, LLC, White Plains, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/971,325

(22) Filed: Dec. 16, 2015

(65) Prior Publication Data

US 2016/0101095 A1  Apr. 14, 2016

Related U.S. Application Data

(60) Division of application No. 14/793,829, filed on Jul. 8, 2015, now Pat. No. 9,307,942, which is a division of application No. 14/453,014, filed on Aug. 6, 2014, now Pat. No. 9,155,502, which is a continuation-in-part of application No. 14/059,541, filed on Oct. 22, 2013, now Pat. No. 8,883,815, which is a continuation-in-part of application No. 14/112,065, filed as application No. PCT/US2012/038312 on May 17, 2012, now Pat. No. 9,089,563, said application No. 14/793,829 is a continuation-in-part of application No. 14/736,406, filed on Jun. 11, 2015, now Pat. No. 9,220,712, which is a continuation-in-part of application No. 14/112,065, filed as application No. PCT/US2012/038312 on May 17, 2012, now Pat. No. 9,089,563.

(60) Provisional application No. 61/487,847, filed on May 19, 2011.

(51) Int. Cl.
| | |
|---|---|
| *A61K 31/435* | (2006.01) |
| *A61K 31/4458* | (2006.01) |
| *A61B 5/00* | (2006.01) |
| *A61K 31/137* | (2006.01) |
| *A61K 45/06* | (2006.01) |
| *A61B 5/055* | (2006.01) |

(52) U.S. Cl.
CPC ........... *A61K 31/4458* (2013.01); *A61B 5/4803* (2013.01); *A61K 31/137* (2013.01); *A61K 45/06* (2013.01); *A61B 5/055* (2013.01); *A61B 5/4064* (2013.01)

(58) Field of Classification Search
CPC ................................................. A61K 31/4458
USPC ....................................................... 514/277
See application file for complete search history.

(56) References Cited

U.S. PATENT DOCUMENTS

| 5,213,553 | A | 5/1993 | Light |
| 6,121,261 | A | 9/2000 | Glatt et al. |
| 8,426,423 | B2 | 4/2013 | Jordan et al. |
| 8,883,815 | B2 | 11/2014 | Roseman |
| 2004/0092605 | A1 | 5/2004 | Jerussi et al. |
| 2006/0052428 | A1 | 3/2006 | Chez |
| 2006/0161218 | A1 | 7/2006 | Danilov |
| 2011/0178114 | A1 | 7/2011 | Aung-Din |

FOREIGN PATENT DOCUMENTS

| CA | 2 342 432 A1 | 9/2002 |
| WO | WO 2010/015029 A1 | 2/2010 |

OTHER PUBLICATIONS

Leitner et al., "Gait in attention deficit hyperactivity disorder", "Effects of methylphenidate and dual tasking", Journal of Neurology, vol. 254, No. 10, pp. 1330-1338 (2007).*
Reorganization after pre-and perinatal Brain Lesions; Martin Staudt; Journal of Anatomy; 2010; pp. 469-474.
New insights into the pathology of white matter tracts in cerebral palsy . . . ; Schecket al.; Developmental Medicine & Child Neurology; Mar. 2012; pp. 684-695.
Pharmacotherapy of Spasticity in Children with Cerebral Palsy; Verrotti et al; Elsevier, Inc. 2006; pp. 1-6.
Speech and Language Therapy for Children with Cerebral Palsy . . . US National Library of Medicine; Jul. 21, 2006; pp. 1-2
Intensive Speech and Language Therapy for Older Children..Cerebral Palsy . . . ; Pennington et al.; Developmental Medicine & Child Neurology; Apr. 2009; pp. 337- 344.
Dopamine Treatment in Children with Cerebral Palsy; Shaare Zedek Medical Center; NIH; May 2011; pp. 1-3.
Perceptual and Articulatory Changes in Speech Production . . . Maria I. Griogs, Ph.D., et al.; J. Med. Speech Language Pathol. 2012; 18(4); pp. 46-53.
Speech Problems Affect More Than one in Two Children With Cerebral Palsy . . . A. Nordberg et al.;ACTA Paediatriaca; 2012; pp. 161-166.
Speech, Expressive Language, and Verbal Cognition . . . with Cerebral Palsy in Iceland; Developmental Medicine & Child Neurology; Jul. 2010; Solveig et al.; pp. 74-80.
Oromotor Variability in Children with Mild Spastic Cerebral Palsy . . . ; Journal of Neuroengineering and Rehabilitation: 2010; Chia-Ling Chen, et al.; pp. 1-10.
Oromotor Dysfunction and Communication Impairments in Children with Cerebral Palsy . . . ; Parkes, et al.; Developmental Medicine & Child Neurology; Jun. 2010; pp. 1113-1119.
Long-Term Survival for a Cohort of Adults with Cerebral Palsy; Hemming Ph.D., et al.; Developmental Medicine & Child Neurology; 2006; 48: pp. 90-95.

(Continued)

*Primary Examiner* — Kevin E Weddington
(74) *Attorney, Agent, or Firm* — Marvin Feldman; Lackenbach Siegel, LLP

(57) ABSTRACT

A methylphenidate, particularly including dextro-threo-methylphenidate, is administered to a child to treat a gait impairment and a speech impairment secondary to a non degenerative disease or disorder acquired in utero, at birth or in infancy, but later manifested.

23 Claims, 11 Drawing Sheets

(56) References Cited

OTHER PUBLICATIONS

Development of the FOCUS, a Communication Outcome Measure for Preschool Children; Thomas-Stonell, et al. Developmental Medicine & Child Neurology; Jun. 2009; pp. 47-53.
Language and Motor Speech Skills in Children with Cerebral Palsy; Pirila, et al.; Journal of Communication Disorders 40: (2007); pp. 116-128.
Survival of Individuals with Cerebral Palsy Born in Victoria, Australia . . . ; Reid, et al.; Developmental Medicine & Child Neurology; Oct. 2011; pp. 353-360.
Factors Associated with Motor Speech Control in Children with Spastic Cerebral Palsy; Chia-Ling Chen, et al.; Chang Gung Medical Journal; vol. 33, No. 4; Jul.-Aug. 2010; pp. 415-423.
Intensive Speech and Language Therapy for Older Children with Cerebral Palsy: A Systems Approach; Penning, et al.; Developmental Medicine & Child Neurology; Apr. 2009; pp. 337-344.
Dysarthria Treatment; Chandramita Bora; Apr. 19, 2010; Buzzle; pp. 1-2.
Speech and Language Therapy for Children with CP might Improve their Communication Skills, but More Research is needed; PubMed Health/NIH; John Wiley & Sons, Ltd. pub. Jul. 21, 2003.
NINDS Cerebral Palsy Information Page; NIH National Institute of Neurological Disorders and Stroke . . . Aug. 21, 2013.
The Effect of Methylphenidate on the Verbal Productivity of Children with Cerebral Dysfunction; Ray O. Creager and Catharine Van Riper; J. Speech Hear Res. 1967:10; 623-628.
Methylphenidate for Giggle Incontinence; Amanda K. Berry et all., The Journal of Urology; vol. 182; Issue 4; Supplement; pp. 2028-2032; Oct. 2009.
Methylphenidate for the Treatment of Gait Impairment in Parkinson's Disease; NIH Clinical Trials; pp. 1-5; Oct. 27, 2009.
PCT/US2012/028212 international search report and written opinion, dated Nov. 7, 2012.
PCT Publication WO 2012/158892 A2; published Nov. 22, 2012.
ISR PCT/US2014/060868, dated Mar. 27, 2015.
Written Opinion PCT/2014/060868, dated Mar. 27, 2015.
Pennington et al., Effects of it Takes Two to Talk, the Hanen Program for Parents of Preschool Children with CP . . . ; Journal of Speech, Language and Hearing Research 52, (5) 1121-1138 (2009).
Effect of Amphetamines of Speech Defects in the Mentally Retarded; Charles H. Fish, MD., MPH, et al. California Medical Association; vol. 96, No. 2, Feb. 1962; pp. 109-111.
Effect of Single Dose Methylphenidate on Walking and Postural . . . Oxford Journals Medicine & Health & Science & Mathematics Journal of Gerontology Series A; vol. 68, Issue 10, pp. 1271-1280 The Biological Sciences and Medical Sciences; Zamir Shorer et al.
Stability and Decline in Gross Motor Function Among Children and youth with Cerebral Palsy . . . , Steven E. Hanna, PhD., Developmental Medicine & Child Neurology, vol. 51, Issue 4, Apr. 2009, pp. 295-302.
Methylphenidate for Cerebral Palsy with Choreoathetois, Willem Boogerd, MD, PhD, ACP, vol. 13, Mar. 21, 2000, pp. 1-2.
Practice Parameter Pharmacologic Treatment of Spasticity in children . . . M.R. Delgado et al., Neurology Jan. 26, 2010; 74(4); pp. 336-343.
[$^3$H] Threo-($\pm$)-Methylphenidate Binding to 3,4-Dihydroxphenylethylamine . . . Properties of Ritalinic Acid Esters; Margaret M. Schwere et al. Journal of Neurochemistry, vol. 45, No. 4, 1985, pp. 1062-1070.
Relative Hydrolytic Rates of Certain Alkyl . . . phenylacetrates; Philip S. Portoghese et al; Journal of Pharmaceutical Science, vol. 50, No. 6, Jun. 1961.
Activity, Activity . . . Approach to Cerebral Palsy; Diane L. Damiano, Physical Therapy, Nov. 2006, vol. 86, No. 11; pp. 1534-1540.
What is Rett Syndrome, National Institute of Neurological Disorders and Stroke, Pub date Nov. 2009 NIH Pub. No. 09-4863; pp. 1-7.
New Methylphenidate Formulations for the Treatment of..disorder; Patrick et al.; Expert Opinion on Drug Delivery;pp. 121-143.
Methylphenidate and its Isomers; Heal et al; CNS Drugs 2006; 20 (9); pp. 713-738.
J.M. Hausdorff et al. Maturation of Gait Dynamics:Stride-to-Stride Variability and its Temporal Organization in Children; American Physiological Society; 199; pp. 1040-1047.
N. Papadopoulos et al. An Investigation of Gait in Children with Attention Deficit Hyperactivity Disorder: A Case Controlled Study; Psychiatry Research 218 (2014); pp. 319-323.
Centers for Disease Control and Prevention; Symptoms and Diagnosis ADHD; Ref: American Psychiatric Association; Diagnostic and Statistical Manual of Mental Disorders, 5$^{th}$ Ed., (2013).

\* cited by examiner

TREATMENT FOR CEREBRAL PALSY GAIT IMPAIRMENT

PRIOR RELATED APPLICATIONS

This application is a divisional application of U.S. application Ser. No. 14/793,829, filed Jul. 8, 2015, which is a divisional application of U.S. application Ser. No. 14/453,014, filed Aug. 6, 2014, now U.S. Pat. No. 9,155,502, which is a continuation-in-part application of U.S. application Ser. No. 14/059,541, filed Oct. 22, 2013, now U.S. Pat. No. 8,883,815, which is a continuation-in-part application of U.S. application Ser. No. 14/112,065, filed Dec. 24, 2013, now U.S. Pat. No. 9,089,563, which is a US 371 National Phase application of PCT/US2012/038312, filed May 17, 2012, which claims priority to U.S. Provisional Application No. 61/487,847, filed May 19, 2011; and This application Ser. No. 14/793,829, filed Jul. 8, 2015, is a continuation-in-part application of U.S. application Ser. No. 14/736,406, filed Jun. 11, 2015, now U.S. Pat. No. 9,220,712, which is a continuation-in-part of U.S. application Ser. No. 14/112,065, filed Dec. 24, 2013, now U.S. Pat. No. 9,089,563, which application is a US 371 National Phase application of Patent Application No. PCT/US2012/038312, filed May 17, 2012, which claims priority to U.S. Provisional Patent Application Ser. No. 61/487,847, filed May 19, 2011, which applications are incorporated herein in their entireties by reference thereto.

FIELD OF THE INVENTION

This invention relates to a pharmaceutical intervention and method for treating a gait impairment, particularly including a gait impairment secondary to cerebral palsy. Specifically, this invention relates to a pharmaceutical intervention for a subject with motor deficits in the limbs. More specifically, this invention also relates to a pharmaceutical intervention for treating gait and speech impairments secondary to cerebral palsy. More specifically, this invention also relates to a pharmaceutical intervention for treating gait abnormalities or impairments resultant side effects of anti-cancer and anti-seizure drugs.

BACKGROUND AND DISCUSSION OF THE PRIOR ART

Cerebral palsy (CP) is a non-progressive disease or disorder involving irreparably damaged or injured areas of the brain, including connections between the cortex and other parts of the brain (the central nervous system) and the muscles in the peripheral nervous system. The National Institute of Neurological Disorders and Stroke (NINDS) of the National Institutes of Health (NIH) defines cerebral palsy as any of a number of neurological disorders that appear in infancy or early childhood and permanently affect body movements and muscle coordination but do not worsen over time, and the NIH makes clear that cerebral palsy cannot be cured.

Infantile cerebral palsy (ICP) refers to a disorder affecting movement. Infantile spastic cerebral palsy refers to ICP with spastic motor defects. Generally, infantile spastic cerebral palsy can be separated into two groups: (1) the symmetric palsies, including the diplegias, which exhibit symmetric involvement on both sides of all four extremities but to a greater degree in the legs, and the paraplegias, in which the lower extremities are equally involved, and (2) the asymmetric palsies which include the hemiplegias, monoplegias, triplegias and quadriplegias. The quadriplegias differ from the diplegias in that all four extremities are more or less irregularly involved often with equal or greater spasticity in the arms.

A most common type of spastic cerebral palsy is spastic diplegia. Most individuals with spastic diplegia exhibit scissors gait. Scissors gait is characterized by adduction and internal rotation at the hip, rigidity and excessive adduction of the leg in swing, flexion at the knee, planton flexion at the ankle and contractions of the spastic muscles. Other cerebral palsy gait impairments include toe down where the toe is pointing down and inward. Such gait impairments result in the toe-to-heel step as opposed to the correct heel-to-toe step. Toe-to-heel step in turn causes considerable pain to the individual. Some individuals may exhibit combinations of such characteristics.

Attempts to treat gait impairments and spasticity include devices such as a therapeutic chair as disclosed in U.S. Pat. No. 4,145,083, issued Mar. 20, 1979 to Urban; transcranial electrode stimulation as disclosed in U.S. Pat. No. 4,844,075, issued Jul. 4, 1989 to Liss; transcranial magnetic stimulation as disclosed in US2011/0270345A1, published Nov. 3, 2011 to Johnston et al.; neurosurgery as disclosed in U.S. Pat. No. 6,936,049, issued Aug. 30, 2005 to Svadovskiy; botulism toxin as disclosed in U.S. Pat. No. 7,378,389, issued May 27, 2008 to Graham; and combinations of botulism toxins with automated movement therapy as disclosed in US 2008/0279896A1, published Nov. 13, 2008, to Heinen et al. Heinen et al. discloses pharmaceutical muscle stimulation prior to and in combination with botulism toxin and in further combination with automated movement interventions.

Parkinson's disease is a degenerative disorder of the cerebral nervous system effecting specific motor systems that result specifically from the dearth of dopamine generating in the basal ganglia. Parkinson's disease is an idiopathic degenerate disorder that develops usually in individuals 60 years of age or older. A brain scan of an individual with Parkinson's' disease reveals no brain damage, unlike cerebral palsy. Parkinson's disease is characterized by stiffness or rigidity, slow and decreased movements resulting in gait instability and the readily recognizable Parkinson's shuffle. Parkinson's gait rigidity is markedly distinguished from cerebral palsy spasticity. Insofar as Parkinson's disease results from a loss of dopamine, one treatment is the administration of dopamine agonists particularly methylphenidate, as disclosed in *Methylphenidate for the Treatment of Gait Impairment in Parkinson's Disease*; NIH Clinical Trials, pp 1-5; Oct. 27, 2009; and dopamine transporter inhibitors, as disclosed in U.S. Pat. No. 8,258,305, issued Sep. 4, 2012 to Hauske.

The art desires a treatment for a cerebral palsy gait impairment in one or both lower limbs that provides persistent improvement in gait and does not require mechanical, electro-mechanical, invasive and toxic interventions.

The art also desires a treatment as aforesaid including a pharmacological intervention and method for treating a gait abnormality or impairment resultant side effect from the administration of an anti-cancer or anti-seizure drug.

The art desires a treatment as aforesaid wherein the impairment is diminished, and the diminishment in the impairment persists and continues over time, even when the pharmaceutical intervention is no longer efficaciously present.

The art also desires a pharmacological intervention as aforesaid for the simultaneous treatment of a gait or limb impairment and a speech impairment, particularly in children, and more specifically including Rett syndrome limb and speech impairments.

The art also desires a pharmacological intervention for a gait impairment as aforesaid that is readily administered, efficacious and safe, with ready and persistent diminishment of the gait abnormality or impairment. The present invention provides a solution to the aforesaid needs.

SUMMARY OF THE INVENTION

The present invention, in one aspect, is a pharmaceutical intervention and method for treating a gait impairment in a subject having cerebral palsy. The method includes administering a therapeutically effective dose of a psychostimulant, particularly a norepinephrine dopamine reuptake inhibitor (NDRI), to the subject to effect gait impairment diminishment.

The present invention, in another aspect, is a pharmaceutical intervention and method for treating a child with a gait impairment with motor deficits in one or both lower limbs. The method includes administering a therapeutically effective dose of a psychostimulant to the subject to effect diminishment of the gait impairment and reduction of the pain associated with the gait impairment. The diminishment of the gait impairment and reduction in pain persists over time even when the psychostimulant is no longer efficaciously present.

The present invention, in one further aspect is the combination of a first medicament that efficaciously treats a disease or disorder but has an adverse side effect of a gait abnormality or impairment and/or a speech impairment, and a second medicament that includes a psychostimulant, wherein the combination of medicaments results in avoided or diminished gait or speech impairments. Gait abnormalities and sensory loss impairments resultant from anti-seizure and anti-cancer medicaments are treated by the present invention.

The invention, in a further specific aspect, is a pharmaceutical intervention and method for treating speech impairments and limb disorders secondary to Rett syndrome. Rett characteristics particularly an apraxia of speech and non specific hand-wringing are diminished with the present pharmaceutical intervention.

The present invention as aforesaid is wherein the pharmaceutical intervention is an NDRI that has mood elevating or anti-depressant properties such as a methylphenidate, particularly including dextro-threo-methylphenidate.

Without wishing to be bound by any theory or mechanism, it is believed that the administered NDRI, particularly including a methylphenidate, and more particularly dextro-threo-methylphenidate, provides or restores neural pathways extending from the prefrontal cortex so as to provide improved management and control of the limbs, particularly the lower limbs in turn resulting in improved or corrected gait.

Without wishing to be bound by any theory or mechanism, it is also believed that the methylphenidates administered pursuant to the present invention may affect or restore neural pathways between upper motor neural lesion areas of the brain and the spine.

BRIEF DESCRIPTION OF THE DRAWINGS

FIG. 2 demonstrates that the GMFCS level number after a regimen of the pharmacological intervention of the present invention is at least one level number less than before the regimen.

DESCRIPTION OF THE INVENTION

Figure 1:
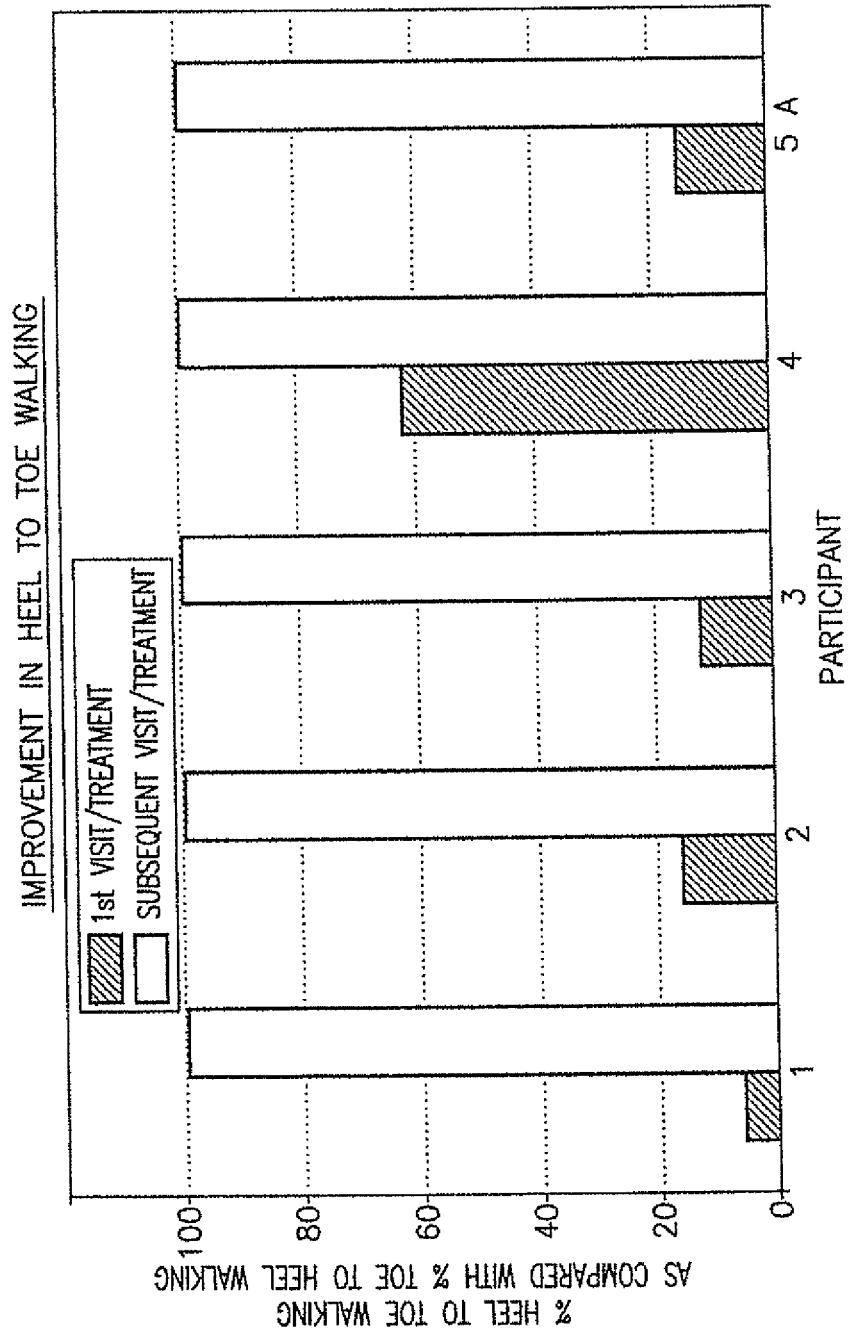
FIG. 1 shows the % heel-toe-toe as compared to % toe-to-heel step gait at the initial administration of a pharmacological intervention of the present invention and at the time of a subsequent administration of a pharmacological intervention pursuant to the present invention for Participants 1-5A.

The term "subject" as used hereinbefore and hereinafter means a human or other mammal, and includes a patient, or a participant in a study or clinical trial.

The term "therapeutically effective dose" or "therapeutically effective dosage" as used hereinbefore and hereinafter means an amount of the administered substance that is sufficient to provide a diminishment of the impairment.

The term "psychostimulant" as used hereinbefore and hereinafter is broadly defined to include an NDRI having antidepressant or mood-elevating properties, and as further discussed hereinafter.

The terms "MPH" and "MPD" as used hereinbefore and hereinafter refer to racemic methylphenidate.

The term or acronym "GMFCS" means Gross Motor Function Classification System. The gross motor skills (e.g. sitting and walking) of children and young people with cerebral palsy can be categorized into 5 different levels using a tool called the Gross Motor Function Classification System (GMFCS). The GMFCS levels are: Level 1 walks without limitations; Level II walks with limitations. Limitations include walking long distances and balancing, but not as able as Level I to run or jump; may require use of mobility devices when first learning to walk, usually prior to age 4; and may rely on wheeled mobility equipment when outside of home for traveling long distances; Level III—walk with adaptive equipment assistance. Requires hand-held mobility assistance to walk indoors, while utilizing wheeled mobility outdoors in the community and at school; can sit on own or with limited external support; and has some independence in standing transfers; Level IV—self-mobility with use of powered mobility assistance. Usually supported when sitting; self-mobility is limited; and likely to be transported in manual wheelchair or powered mobility; and Level V—severe head and trunk control limitations. Requires extensive use of assisted technology and physical assistance; and transported in a manual wheelchair, unless self-mobility can be achieved by learning to operate a powered wheelchair.

The terms "visit", "examination" or "visit/examination" refer to an examination of the Participant by a pediatric neurologist.

The present invention includes the administration of a therapeutically effective dose of one or more of a broad range of NDRIs or dopamine agonists including a methylphenidate, particularly including dextro-threo-methylphenidate, (Focali®), and the non linear lower alkyl phenidates, particularly including isopropylphenidate.

The present invention treats subjects, particularly children, diagnosed with cerebral palsy having secondary disorders including both a gait impairment and a speech impairment. The treatment of speech impairment secondary to cerebral palsy is disclosed in co-pending application Ser. No. 14/453,014, filed Aug. 6, 2014, and in parent application Ser. No. 14/059,541, filed Oct. 22, 2013, now U.S. Pat. No. 8,883,815, which references are incorporated herein in their entireties by reference thereto.

The present invention contemplates a combination of two medicaments, a first medicament that efficaciously treats a certain disease or disorder but has an adverse side effect, namely a gait abnormality or impairment and/or speech impairment, and a second medicament namely a psychostimulant having mood elevating or anti-depressant properties, particularly including a methylphenidate, that diminishes the gait or speech impairment. The first medicament is typically an anti-cancer or anti-seizure medicament.

It is widely reported that anti-seizure medicaments including oxcarbazepine (Trileptal®) and cancer treatment medicaments including thalidomide, thalidomide analogs and Abraxane® have adverse side effects leading to a pronounced percentage of gait abnormalities or impairments and to a much lesser percentage of speech impairments. Anticancer drug-induced peripheral neurotoxicities are predominately sensory. Sensory loss in the feet and legs can in turn cause sensory ataxia and gait abnormalities or impairments. It is within the contemplation of the present invention to combine or co-administer the pharmaceutical intervention of the present invention with a anti-seizure or cancer medicament.

The art suggests thalidomide can also be used in the treatment of ALS, as disclosed in US Pub. 2005/0182097, published Aug. 18, 2005 to Zeldis et al. Speech impairments are secondary to ALS. The present pharmaceutical intervention may likewise be used in the thalidomide treatment of ALS It is also within the contemplation of the present invention to combine or co-administer thalidomide, thalidomide analogs or Abraxane® with the psychostimulant of the present invention, particularly methylphenidate, and more particularly dextro-threo-methylphenidate, to efficaciously treat the cancer or ALS while diminishing or precluding the gait and speech impairments.

It has been surprisingly found that the pharmaceutical intervention and method of the present invention diminishes the aforesaid impairments, which diminishment in impairments and pain persists even when the pharmaceutical intervention is no longer efficaciously present.

Examples

Participant 1

Participant 1 is a male and was 8 years old at the time of the first pharmacological intervention pursuant to the present invention. Participant 1 had delayed speech and language. Participant 1 was diagnosed as having spastic dipligea, bilateral contractures at the hips. Participant 1 wore leg braces prior to the pharmacological intervention, and the braces were removed in the initial visit. Prior to the pharmacological intervention of the present invention, Participant 1 was treated with Botox injections, oral baclofen and orthotics. The parents of Participant 1 stopped all such treatments because they did not observe any improvement in gait.

Figure 2:
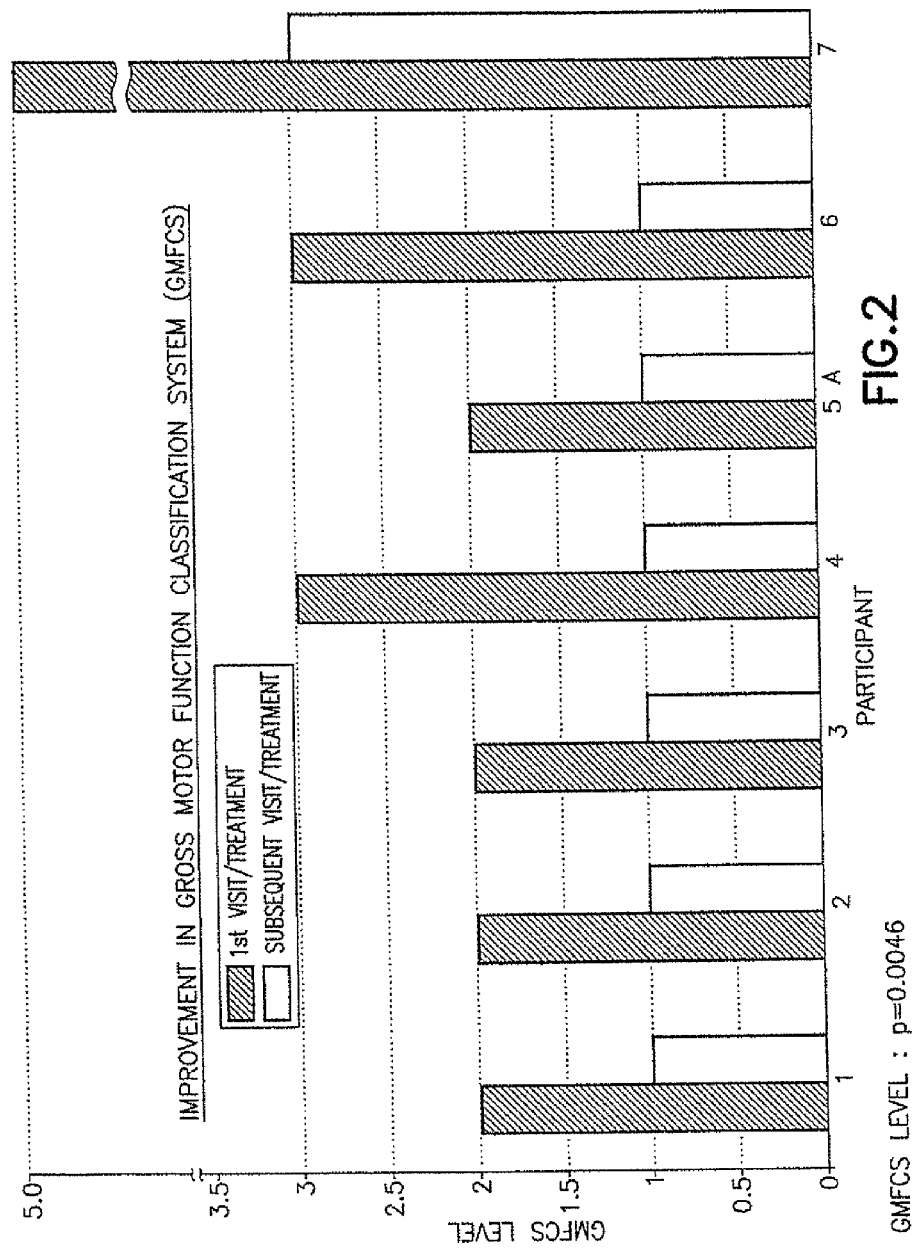
FIG. 2 shows the GMFCS level at the initial time prior to and after a pharmacological regimen of the present invention for Participants 1-7.

The initial pharmacological intervention was 2 cc (10 mg) of Quillivant XR®, and one month later was replaced with 5 mg of racemic methylphenidate (MPD)/day. FIGS. 1-2 for Participant 1 shows the improvement in gait after about 45 minutes at the initial visit, and after daily treatments of 5 mg methylphenidate/day.

Participant 2

Participant 2 is a female and was 15 years old at the time of the initial pharmacological intervention pursuant to the present invention. Participant 2 did not start to walk until 18 months of age, and had significantly delayed speech and language development. She was not speaking in sentences until she was 5 years of age.

Participant 2 was diagnosed with spastic dipligea and painful gait. Her weight increased because of the avoidance of walking to preclude the concomitant pain.

After about one year of daily methylphenidate administrations, she could walk on a flat surface and up and down stairs with flexibility, even when the methylphenidate is no longer efficaciously present in the body.

Participant 2 reports she is pain free, has entered the school talent show and exhibits a 15 minute dance routine performed at school.

Participant 3

Participant 3 is a female and was about 15 years of age at the first pharmacological intervention pursuant to the present invention.

Participant 3 had an initial diagnosis of cerebral palsy, epileptic encephalopathy, global development delay, left hemiplegia and spastic dipligea, left greater than right. At the initial visit, Participant 3 was physically examined and found to have a limited amount of receptive and expressive language, with the left side of the body much smaller than the right side, left hemiplegia, contractions of the left elbow, and unable to open left hand, with the fingers and thumb kept in fisted position. Participant 3 loses balance and falls if not assisted when rising from a chair. When walking on a flat surface, she keeps her left elbow at 90 degrees, left hand remains in a fisted position, toe-to-heel gait, bilateral left greater than right. And to avoid tripping over her left foot, she keeps her left foot in extension securing her left leg as far away from her trunk in order for her left foot to have enough clearance to avoid first hitting the ground with the extremities.

A 400 mg/day Gabapentie regimen was prescribed. After 2 months, there was a 5 mg MPD initial administration. This was followed by 5 mg MPD/day for a period of 11 months. FIGS. 1-2 show Participant 3 gait improvement at the initial intervention, and after the 11 months of the foregoing regimen.

Participant 3 reports playing sports, even when the MPD is no longer efficaciously present.

Participant 4

Participant 4 is a female, and was about 19 years of age at the time of first pharmacological intervention of the present invention. Participant 4 was born prematurely at 24 weeks. Participant 4 had a twin. The twin died on day one. Participant 4 suffered hypoxia at birth. Participant 4 first began to walk and talk well over 2 years of age. Participant 4 was diagnosed with cerebral palsy and global developmental delay, Hashimoto's thyroiditis, epilepsy, scoliosis and spastic dipligea. An MRI of the brain revealed periventricular leukomalacia. The initial visit revealed that Participant 4 walks with a crouched gait, flexed at the hips and knees, lateral fixed contractions, and obligated toe to heel gait with pain when walking and calf muscular pain when not walking. Medication administered long prior to and during the pharmacological intervention of the present invention included the anti-seizure medicament oxcarbazepine (Trilepal®). Oxcarbazepine (Trilepal®) is reported to cause gait abnormalities as a side effect.

The improvements in gait and step after the two weeks of daily MPD administration are shown in Table 1.

TABLE I

| Heel-to-Toe/<br>Toe-to-Heel (Sec./Sec.) | | Stairs Holding to Railings Up<br>(Sec./Sec.) | | Stairs Holding Railings Down<br>(Sec./Sec.) | |
|---|---|---|---|---|---|
| Initial | 9.38/15 | Initial | 7.4/59 | Initial | 12.81/59 |
| After 2 Weeks | 15/15 | After 2 Weeks | 0/60 | After 2 Weeks | 0/60 |

Participant 4 Example demonstrates improvements in gait including step with co-administration of an anti-seizure medicament having a gait impairment side effect.

It is within the contemplation of the present invention to combine the present pharmacological intervention with a medicament for treating a disease or disorder but with gait abnormality or impairment side effects, whereby the disease or disorder is treated and the impairment side effects are precluded or diminished, particularly as demonstrated in the Participant 4 Example.

Participant 5A

Participant 5A is a female 13 years of age at the time of the first examination pursuant to the present invention. Participant 5A has an identical twin; hereinafter referred to as Participant 5B. Participants 5A and 5B were born to a drug addicted alcoholic woman and were diagnosed with speech and gait impairments secondary to cerebral palsy. Participant 5A had a speech-language disorder and spastic diplegia. Participant 5A had to direct both legs in extension to avoid tripping over her own feet because she was unable to flex and extend at the ankle joint to move her feet, resulting from the spastic dipligea.

At the first visit/treatment, 5 mg of methylphenidate was administered to Patient 5A. Prior to the administration, Participant 5A had no heel-to-toe functionality. After administration, Participant 5A had generally 43% heel-to-toe walking time in both feet in walking and up and down stairs. See FIG. 1. Participant 5A reported no pain after walking.

Figure 3:
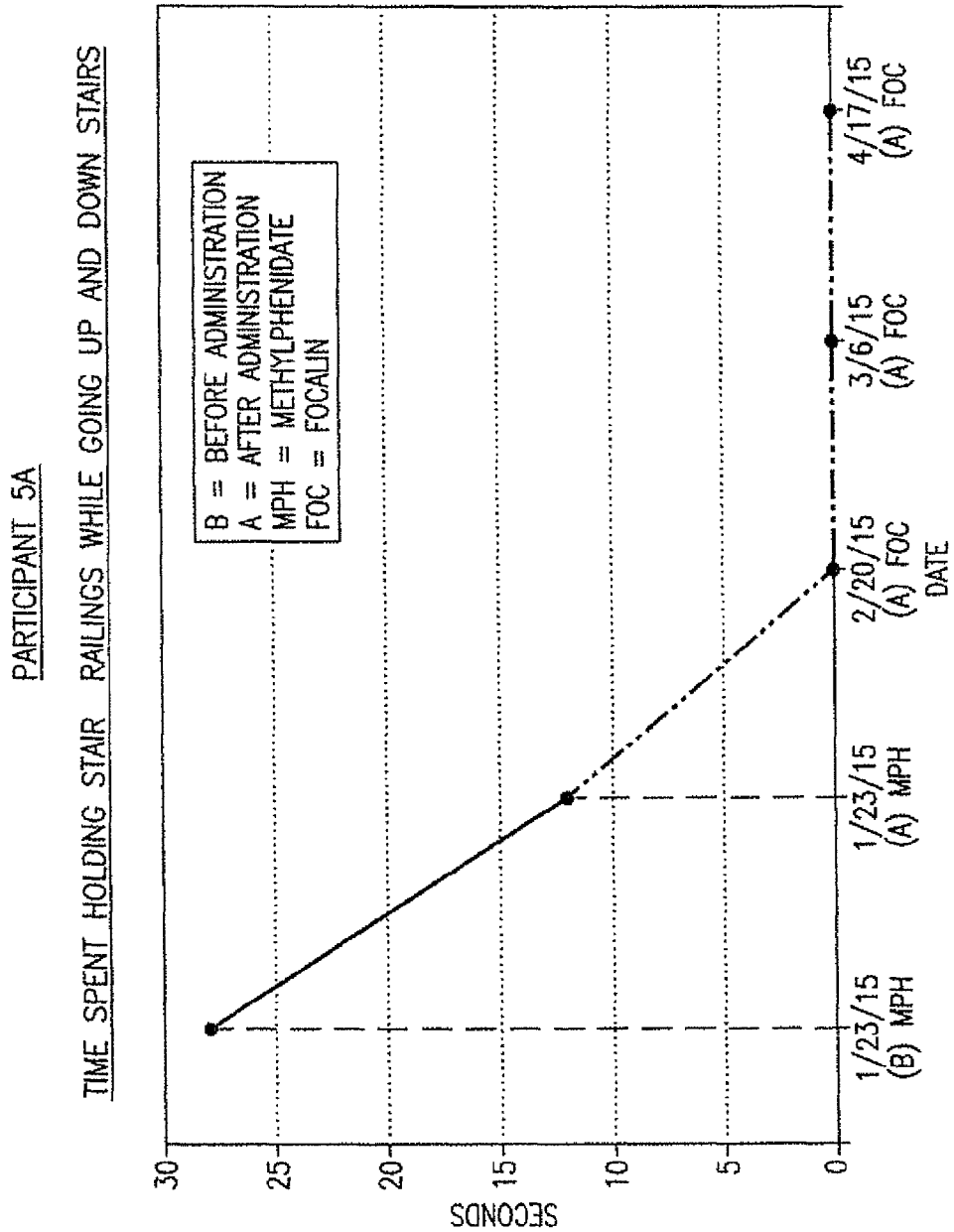
FIG. 3 is a graph of the time spent holding stair railings while going up and down stairs in an initial visit/examination before and after pharmaceutical intervention, and in subsequent visits/examinations for Participant 5A. The solid line is the within the hour measurements at a specific visit/examination, and the broken line is the timeframe between visits/examinations.
Figure 4:
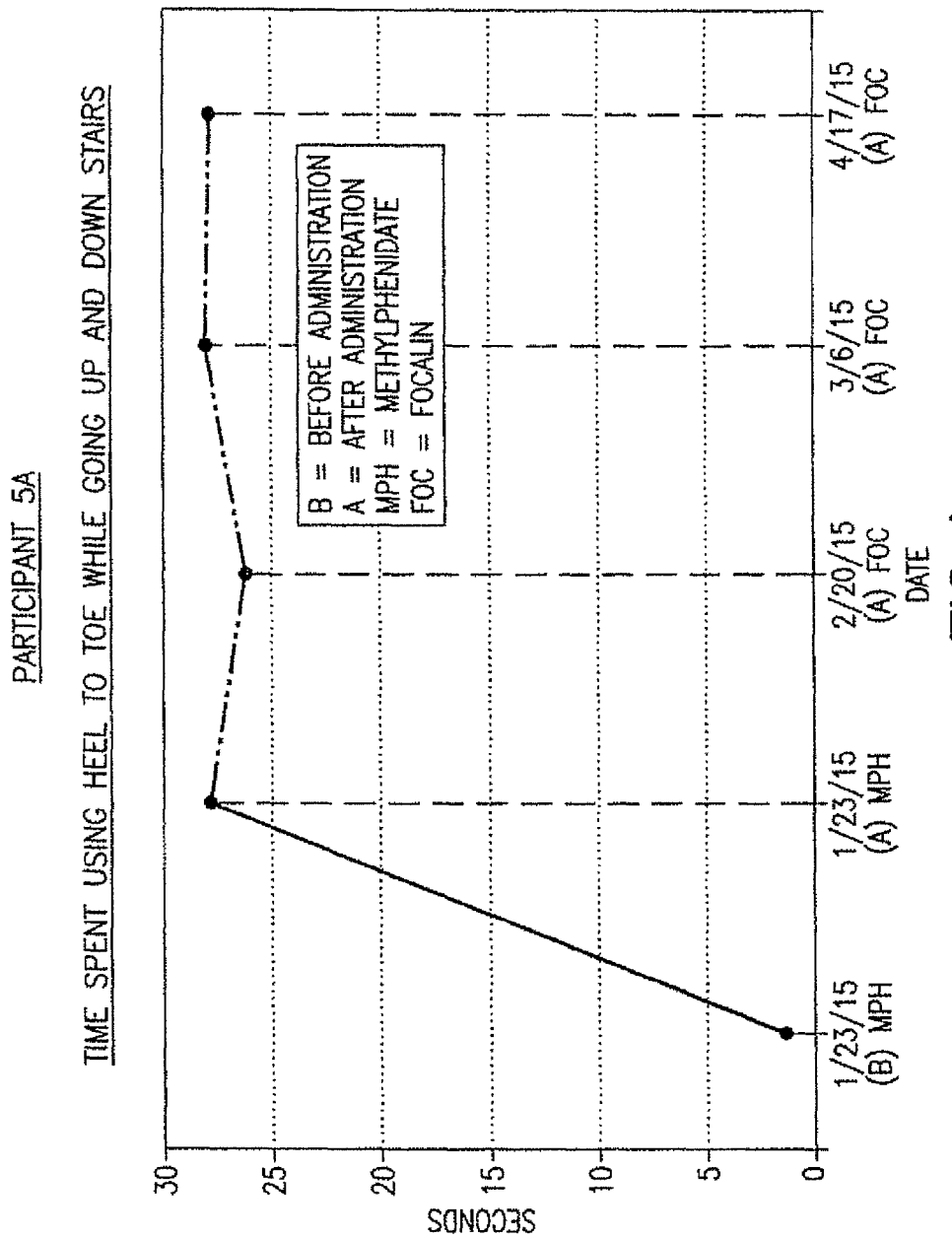
FIG. 4 is a graph of the time spent in a 30 second timeframe in heel-to-toe walking while going up and down stairs at an initial visit/examination before and after the initial pharmaceutical intervention, and in subsequent visits/examinations for Participant 5A. The solid line is the within the hour measurements at a specific visit/examination, and the broken line is the timeframe between visits/examinations.
Figure 5:
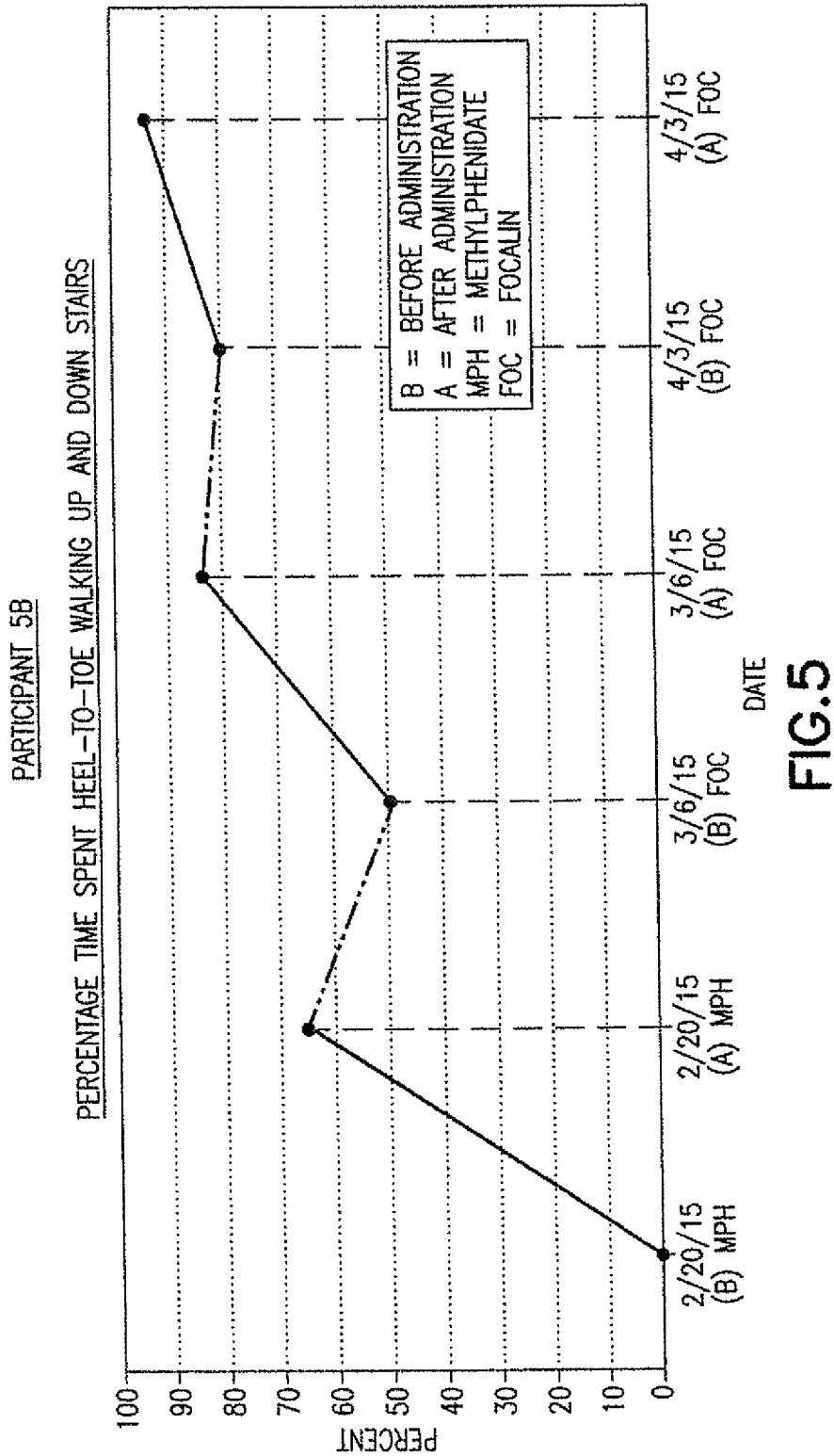
FIG. 5 is a graph of the percentage time in correct heel-to-toe gait when walking up and down stairs in an initial visit/examination before and after the initial pharmaceutical intervention and in subsequent visits/examinations for Participant 5B.

Referring specifically to FIGS. 3 and 5, there is shown the dramatic improvement in heel-to-toe steps in traversing stairs, for Participant 5A, particularly with a Focalin® regimen in lieu of a racemic methylphenidate regimen.

Participant 5B

Participant 5B is the identical twin of Participant 5A. Participant 5B was diagnosed with severe speech impairment secondary to cerebral palsy. Participant 5B, unlike her twin sister, Participant 5A, did not have quite as severe gait impairment. Participant 5B, however, could not keep her foot straight and had to hold onto railings ascending or descending stairs.

In the first examination, because the speech impairment was so severe, Participant 5B was diagnosed as mentally retarded. There was no volitional speech. Participant 5B could not read or comprehend at a second grade level.

In the second examination, a regimen of 5 mg MPD/day was prescribed, to be taken before school.

At the beginning of the third examination, about one month after the second examination, 5 mg MPD was administered. After 40 minutes, Participant 5B had spontaneous speech of 4-6 words, as opposed to the 2-3 word capability in the first examination. Participant 56 comprehended at a second grade level. A revised regimen of 10 mg MPD/day before school was prescribed.

A fourth examination occurred approximately one month after the third examination. Participant 5B was administered 10 mg Focalin®. After 40 minutes, Participant 5B was able to keep her foot straight in walking and did not feel like she was going to fall.

Participant 56 had a regimen of 10 mg/day Focalin® for the next 14 days. A fifth examination was undertaken after the 14 days of Focalin®. At the beginning of the fifth examination, a 10 mg dose of Focalin® was administered. After 45 minutes, Participant 56 had a complete understanding of a book that demonstrated comprehension at a $7^{th}$ grade level. This level of comprehension persisted even when the Focalin® was no longer efficaciously present.

Figure 6:
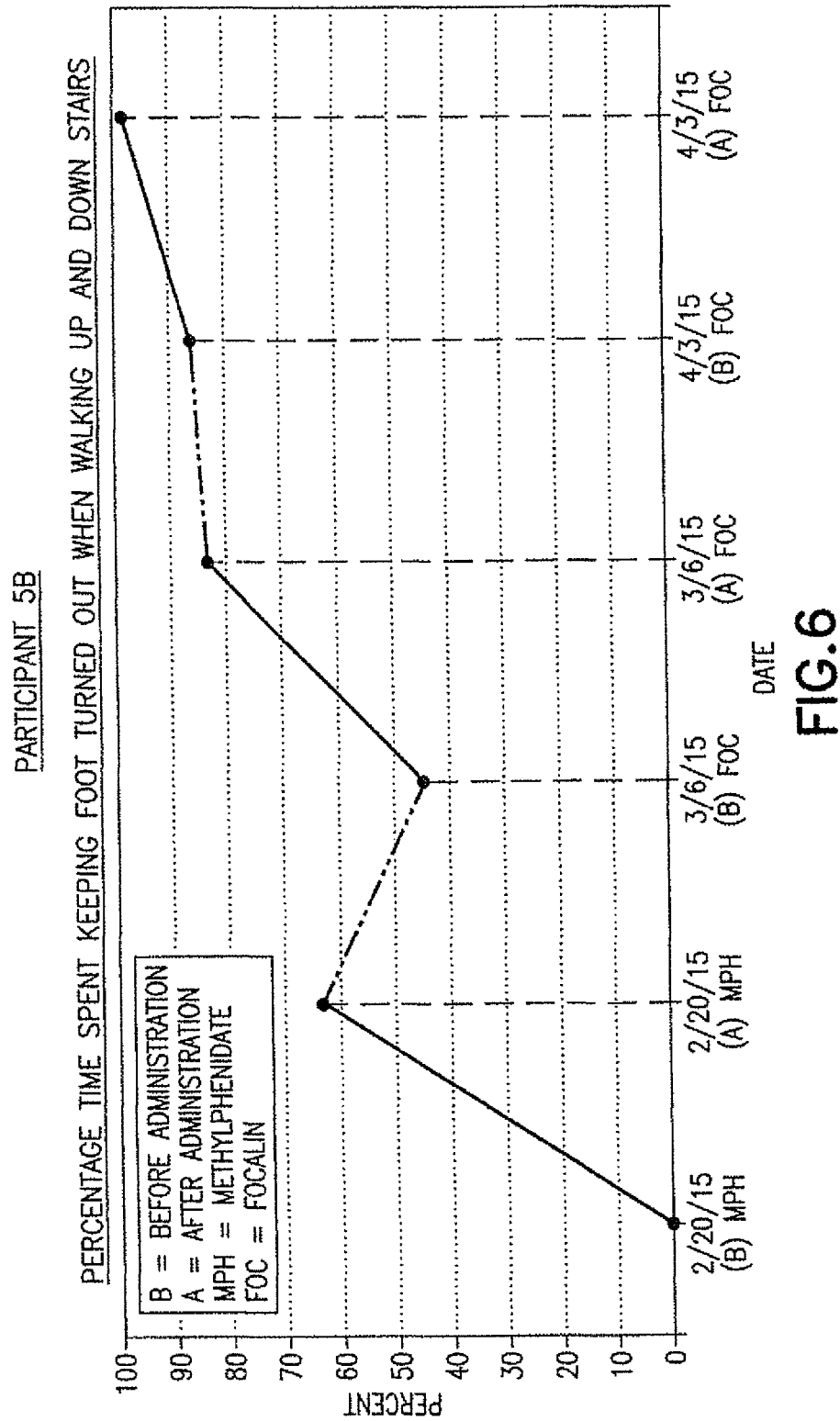
FIG. 6 is a graph of the percentage time spent keeping the foot turned out when walking up and downstairs in an initial visit/examination before and after the initial pharmaceutical intervention and in subsequent visits/examinations for Participant 5B.

Referring specifically to FIG. 6, there is shown the improvement in the percentage time keeping the foot turned outwardly as opposed to inwardly toe down, in traversing stairs for Participant 5B. The improvement is most dramatic with a Focalin® regimen in lieu of a racemic methylphenidate regimen.

The Participants 5A and 5B Examples demonstrate diminishments in both speech and gait impairments secondary to cerebral palsy. The improvements in gait speech and comprehension were particularly significant with a regimen of daily administrations of Focalin®.

Participant 6

Participant 6 is a female. At 2-3 years of age she was diagnosed with cerebral palsy.

Participant 6 had an initial visit or examination when she was 8 years old. A gait impairment, constant hand wringing and an apraxia of speech were observed. The gait impairment was a scissors gait with the ankle turning inwards and crossing over when walking.

A 5 mg MPD dose was administered to Participant 6. After 40 minutes, there was a noticeable improvement in gait. A regimen of 5 mg MPD/day was prescribed and continued for one year, at which time the dose was increased to 5 mg MPD/twice daily; once after breakfast and once after lunch. Observations for Participant 6 in subsequent visits/examinations are reported in the FIGS. 6-9, and were taken when Participant 6 was off MPD for 24 hours.

In the course of the afore-described treatment, a genetic work-up was prescribed. It was determined that Participant 6 had a polymorphism heterozygote genetic defect, namely a mutant MECP2 gene. Consequentially she was diagnosed as having Rett syndrome. Participant 6 was observed as having a motor apraxia. She exhibited constant nonspecific hand-wringing consistent with Rett syndrome.

Rett syndrome is a neurodevelopment disorder that affects girls almost exclusively. In nearly all cases of Rett syndrome, there is a mutation in the methyl CpG binding protein 2, or MECP2 gene. The symptoms are generally overlooked in the early stages. As the syndrome progresses, the child has jerkiness in limbs and gait impairments, and the child loses purposeful use their hands, characterized as constant hand washing or hand-wringing. In later stages, apraxia and particularly an apraxia of speech occur. There is no known cure for Rett syndrome, and the life expectancy at best is about 40 years, as reported in the NIH National institute of Neurological Disorders and Stroke (NINDS) "Rett Syndrome Fact Sheet," NINDS Pub. November 2002, updated Feb. 23, 2015.

Figure 7:
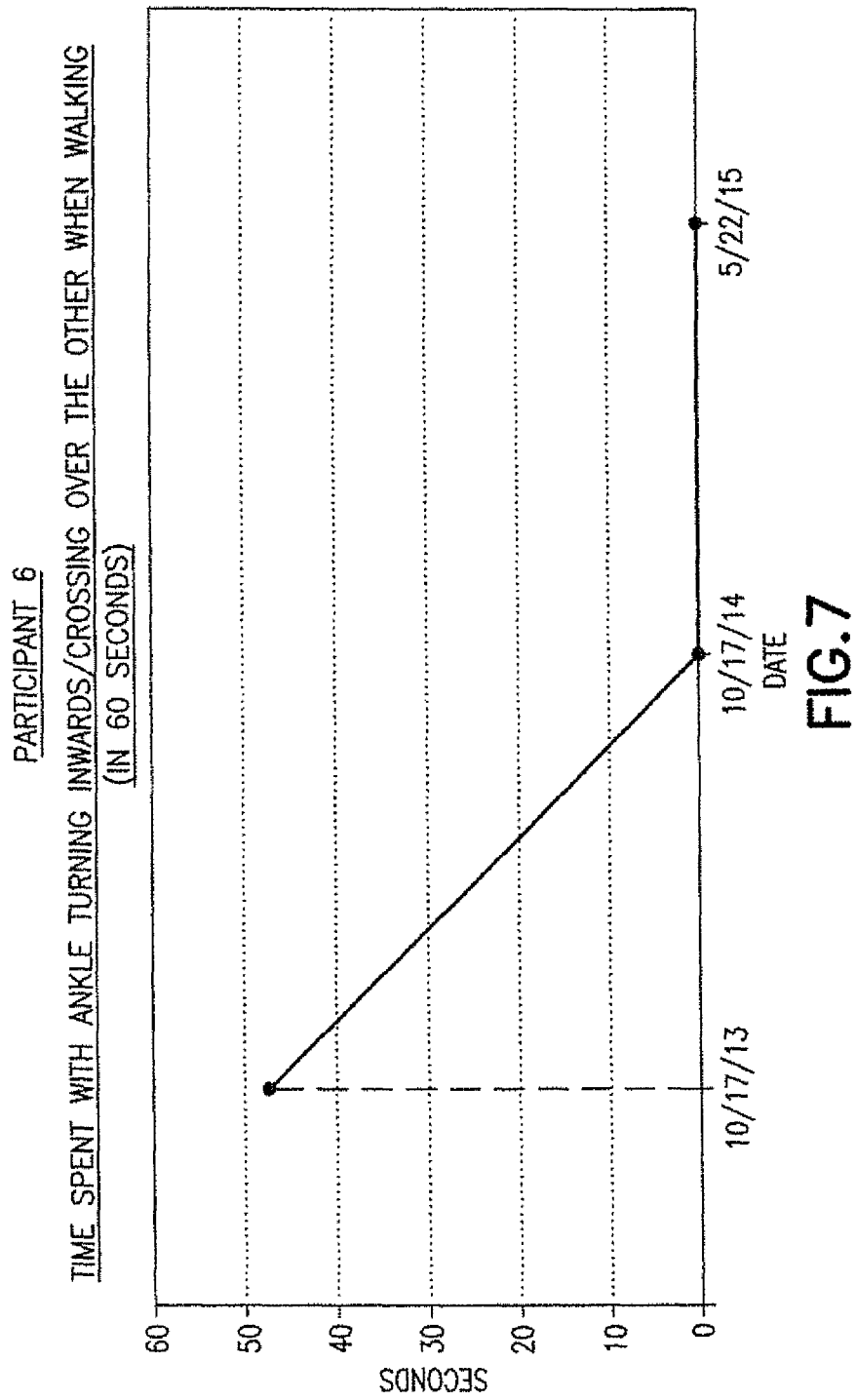
FIG. 7 is a graph of the time spent in seconds over a 60 second timeframe with the ankle turned inwards and crossing over the ankle when walking in an initial visit/examination and in subsequent visits/examinations for Participant 6.
Figure 8:
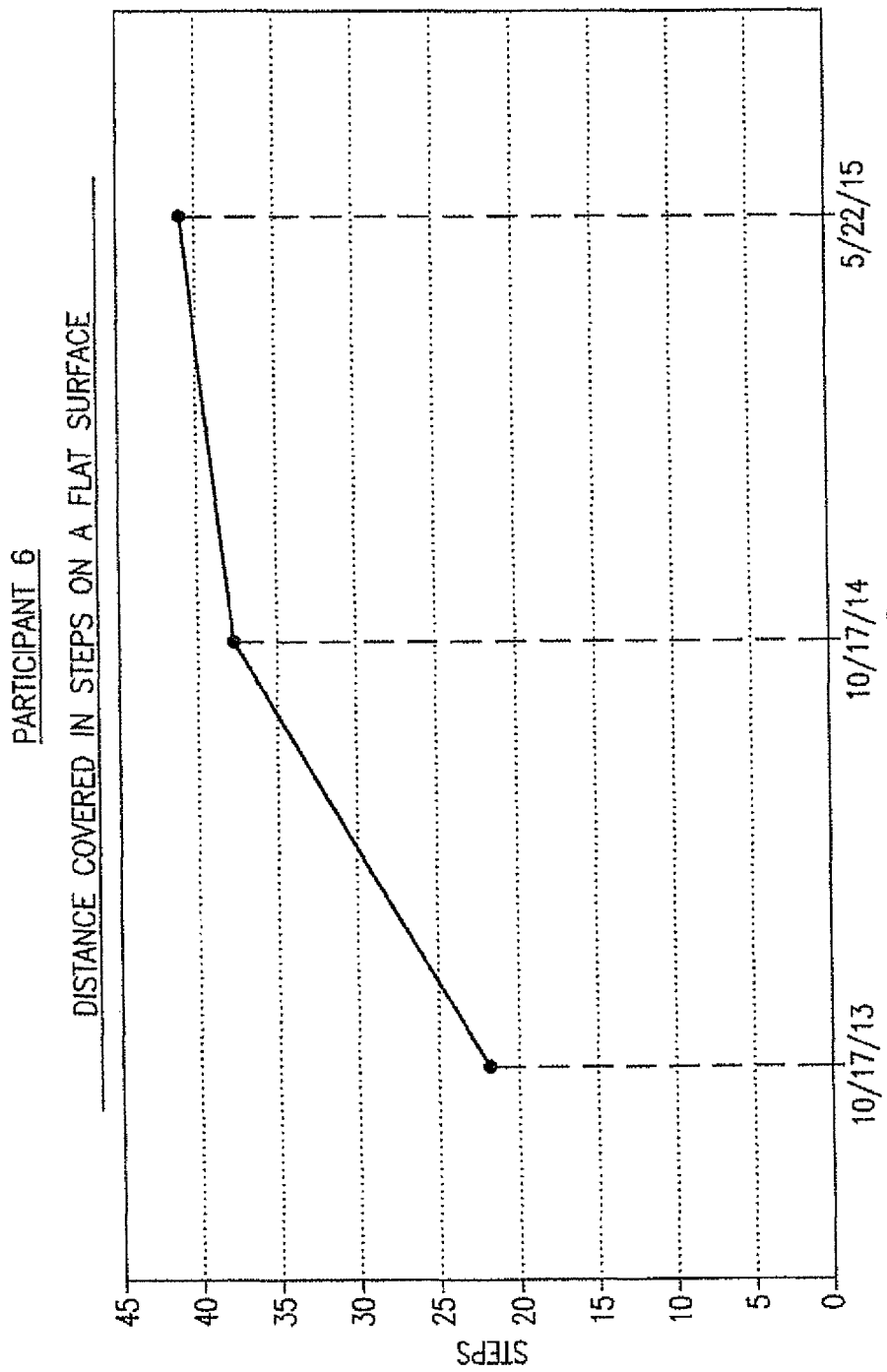
FIG. 8 is a graph of the distance covered in steps walking on a flat surface attempting to traverse a course at an initial visit/examination, and traversing the course in subsequent visits/examinations for Participant 6.
Figure 9:
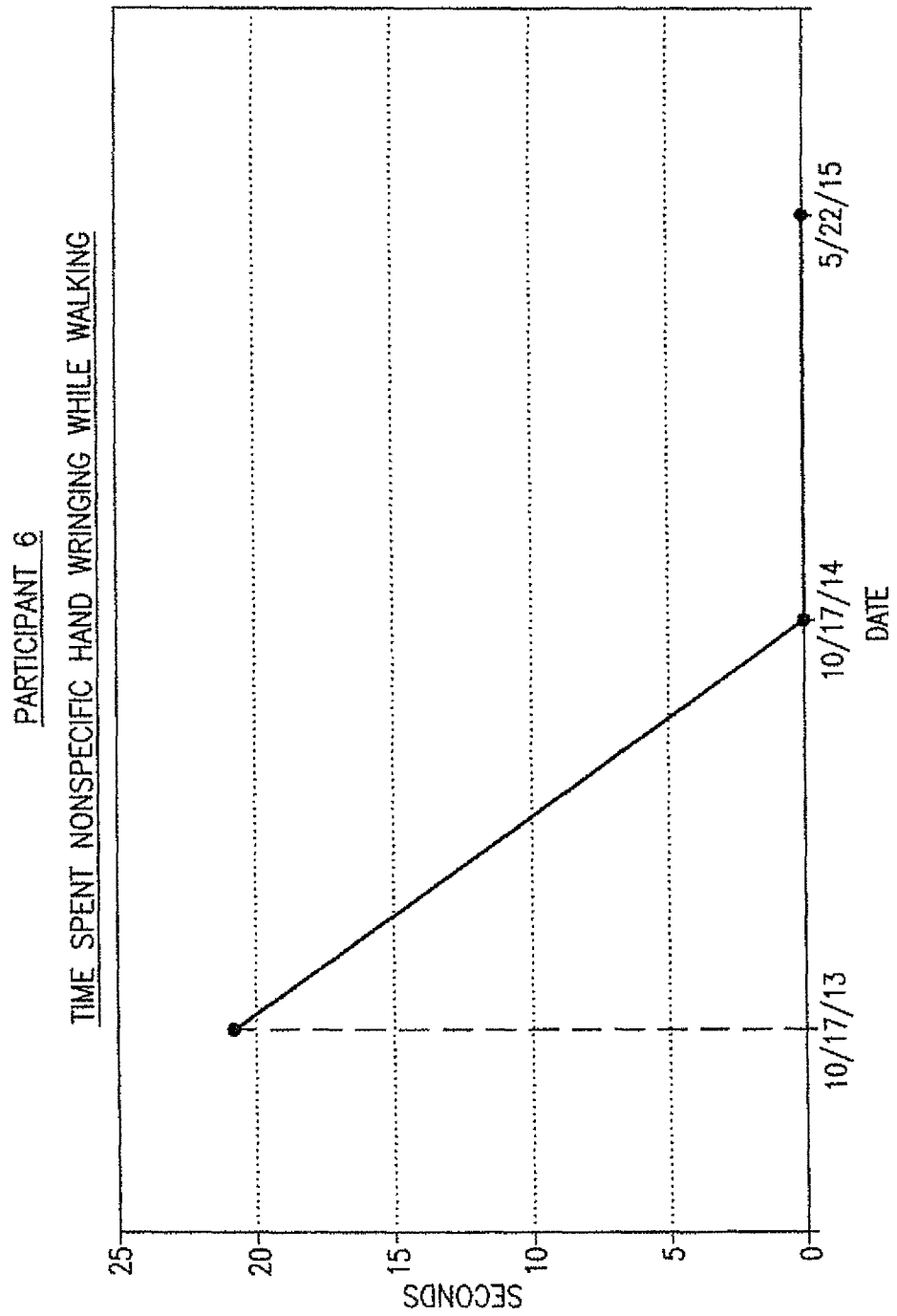
FIG. 9 is the time spent in nonspecific hand wringing while walking measured at visits/examinations during the pharmacological intervention regimen for Participant 6.

Referring specifically to FIGS. 7-9, there is shown the improvement in gait for Participant 6 in an MPD regimen over the course of a two year period. Participant 6 showed continued improvement in motor planning and execution, particularly the elimination of ankle inwards and toe down impairments. Prior to Oct. 17, 2013, Participant 6 was able to traverse only 25 feet in 60 seconds, and by May 22, 2015, Participant 6 was able to traverse 66 feet in 60 seconds. These improvements resulted from the diminishment in motor apraxia and elimination of the nonspecific hand-wringing while walking.

As demonstrated in FIG. 2 and FIGS. 7-9, the MPD course of treatment resulted in a GMFCS improvement from level number 3 to level number 1, essentially a complete diminishment of scissors gait and an essentially complete diminishment of the hand-wringing. Speech language equivalence improved dramatically over the course of treatment evidencing or diminishment of the apraxia of speech.

The Participant 6 Example demonstrates the pharmaceutical treatment of limb impairments, particularly including nonspecific hand wringing and an apraxia of speech secondary to Rett syndrome.

Participant 7

Participant 7 is a female born in 2004. The first examination was when Participant 7A was about 3 years and 4 months of age. Participant 7 had no speech. Participant 7 was diagnosed with bilateral ankle clonus, bilateral Babinski and spastic dipligea. Participant 7 was in a wheelchair. An MRI revealed brain damage consistent with cerebral palsy.

The second examination was when Participant 7 was 4½ years of age. Participant 7 remains in a wheelchair. Participant 7 was able to move her legs but not sequentially while sitting in the wheelchair. Participant 7 has leg braces.

The third examination determined that Participant 7 is not healing well because of the continued wearing of the leg braces.

The fourth examination was about three years after the third examination. Participant 7 is about 8 years of age. One month prior to the fourth examination, Participant 7 was prescribed 5 mg MPD/day. At the fourth examination, 5 mg MPD was administered. Participant 7, with assists, was able to get out of the wheelchair and had a somewhat more appropriate posture. A regimen of 5 mg MPD in the morning and in the evening was prescribed.

The fifth examination was one month after the fourth examination. It was reported by the mother and caretakers that Participant 7 was speaking more than she had in the prior month. Participant 7 shows further improvement in moving her legs in the wheelchair. The braces remain.

The sixth examination is one month after the fifth examination. Participant 7 is speaking more. The braces remain.

There is then a 2½ year hiatus during which there are no further examinations or pharmaceutical administrations pursuant to the present intervention. The examinations resumed after the 2½ year hiatus.

At the eleventh examination, the braces remain and appear to have been in place essentially during the entire 2½ year hiatus. There were brace marks on her legs as a result of the extended usage. The Participant 7 legs became weaker. The Participant 7 sedentary life style in turn caused worsened or exacerbated pain in attempts to get out of the wheelchair and stand, and then walk with a walker.

In the course of subsequent visits (examinations $12^{th}$ and $13^{th}$), in a period of about one month, Participant 7 was on a daily dosage regimen of 5 mg MPD, and then 5 mg Focalin®. Two weeks after the eleventh examination, it was agreed to remove the braces permanently. Two weeks thereafter, when Participant 7 had no longer been on MPD for 24 hours, Participant 7A exhibited the ability to stand up from the wheelchair with greater ease, to more readily walk and turn with a walker. She was more able to lift her feet and was less prone to tripping.

Figure 10:
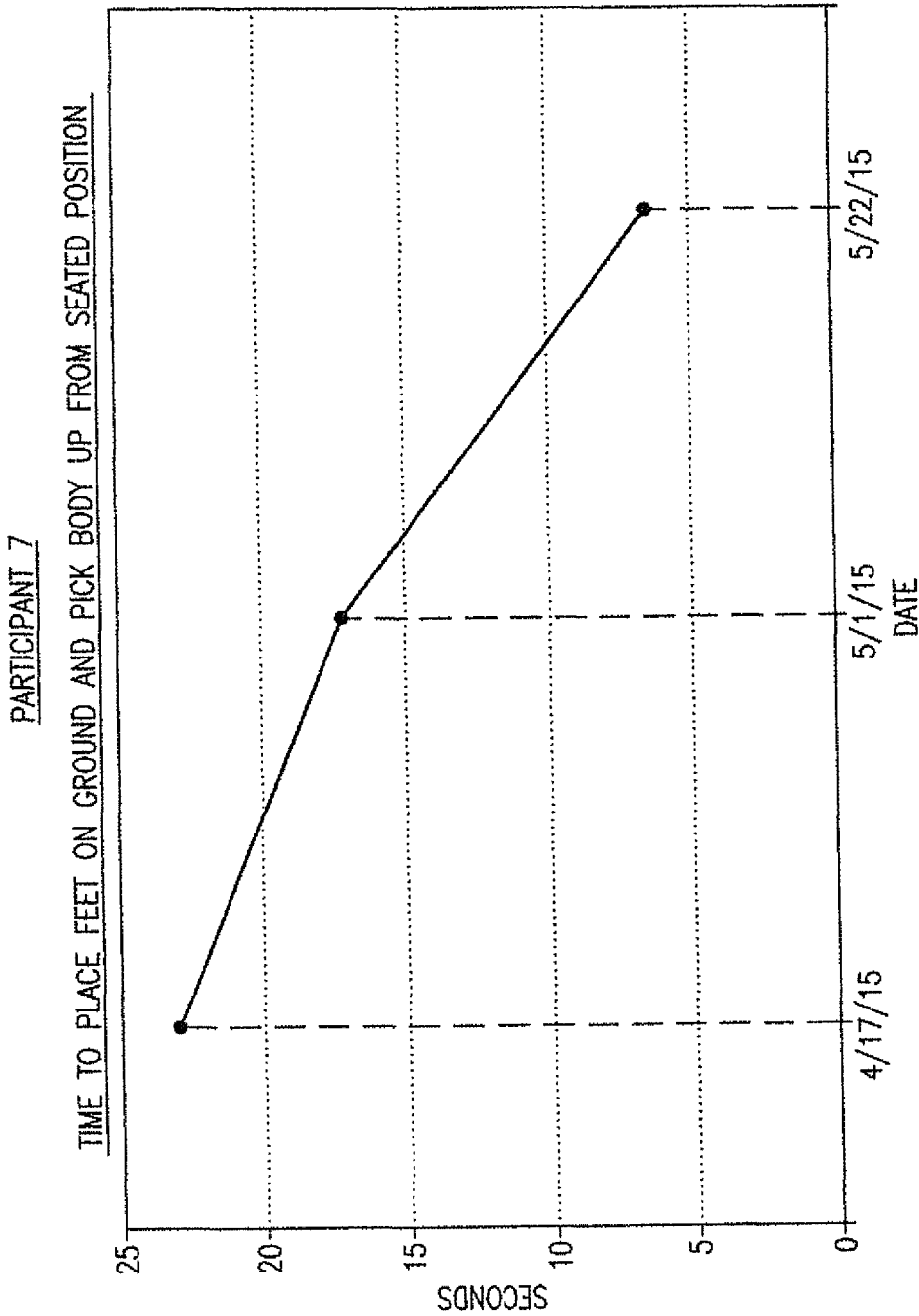
FIG. 10 is a graph of the time to place the feet on the ground and pick the body up from a seated position to standing with a walker in visits/examinations for Participant 7.

FIG. 10 shows the time spent (in seconds) unassisted in standing up from the wheelchair to a walker for Participant 7 during the $11^{th}$ (Apr. 17, 2015), $12^{th}$ (May 1, 2015), and $13^{th}$ (May 22, 2015) examinations.

Figure 11:
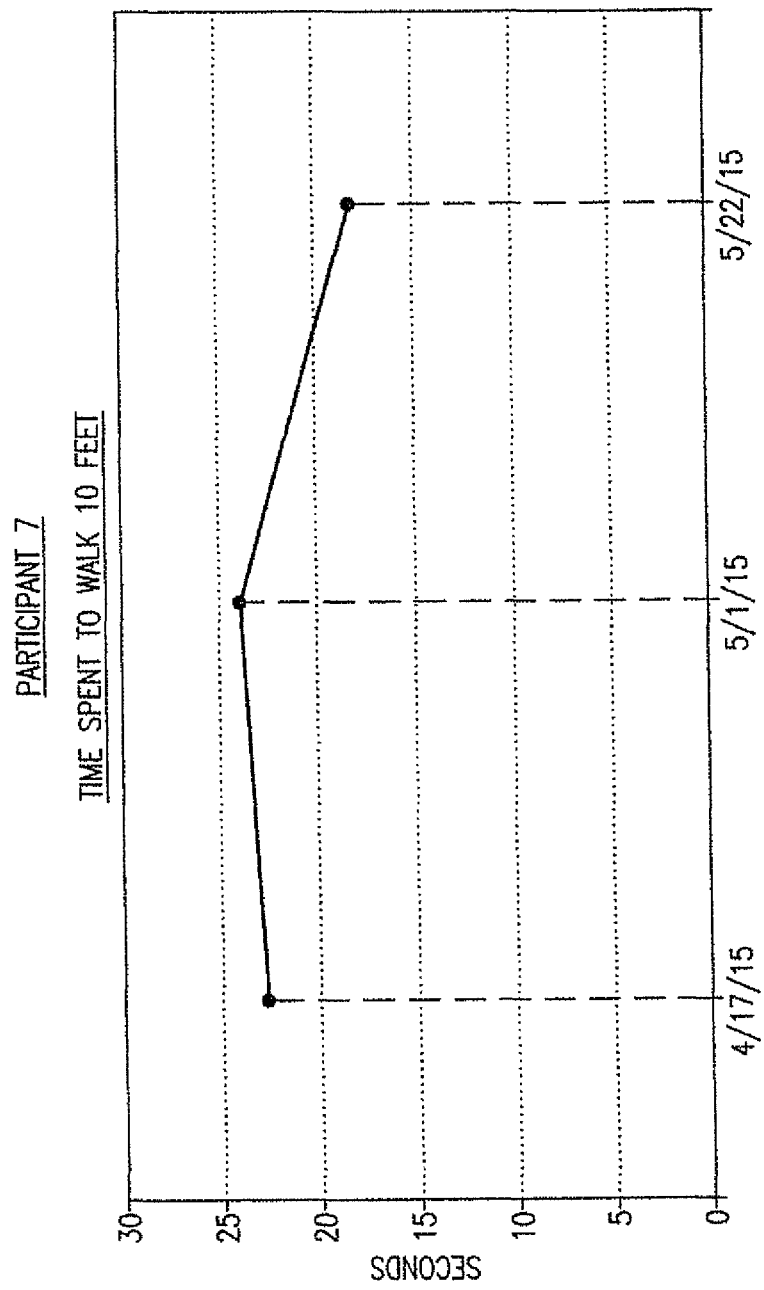
FIG. 11 is a graph of time spent to walk 10 feet during the course of the pharmacological interventions for Participant 7.

Referring specifically to FIGS. 10 and 11, Participant 7 was on a regimen of 5 mg/day Focalin® in a period from the May 1, 2015 visit/examination to the May 22, 2015 visit/examination. FIGS. 10 and 11 demonstrate the dramatic improvement with a Focalin® regimen over about a three week period.

The Participant 7 Example demonstrates that a sustained regimen of MPD and particularly Focalin, with the removal of leg braces, effected significant diminished impairment, particularly the ready ability to lift out of a wheelchair and use in a walker without tripping.

Participant 7 had accordingly improved from a level 5 GFMCS to a level 3 GFMCS as shown in FIG. 2. This is a surprising and unexpected result inasmuch as generally a child at GFMCS level 5 will not improve but remain at a GFMCS level 5.

Particularly suitable psychostimulants pursuant to the present invention include the norephinephrine-dopamine reuptake inhibitors (NDRIs) including, by way of example, methylphenidate, modafinil, armodafiml and dextro-methylphenidate, as discussed in co-pending application PCT/US2012/038312, filed May 17, 2012, and U.S. Ser. No. 14/112,065, filed Oct. 16, 2013, incorporated herein by reference thereto. Extended release, controlled release and immediate release forms methylphenidate are contemplated as useful psychostimulants. Immediate release methylphenidate is a preferred psychostimulant.

Preferred psychostimulants further include the lower alkyl phenidates, such as disclosed in Schweri et al., [$^3H$] Threo-(±)-*Methylphenidate Binding to 3,4-Dihydroxyphenylethylamine Uptake Sites in Corpus Striatum: Correlation with the Stimulant Properties of Ritalinic Acid Esters*, J. of Neurochemistry, vol. 45, no. 4, pp. 1062-70, (1985), and Portoghese et al, *Relative Hydrolytic Rates of Certain Alkyl (b) dl-a-(2-Piperidl)-phenylacetrates*, J. Pharmaceutical Science, vol. 50, no. 6, pp. 494-51, and U.S. Pat. No. 6,528,530, issued Mar. 4, 2003 to Zeitlin, et al. Preferred psychostimulants also include the nonlinear lower alkyl phenidates, namely isopropyl, isobutyl, d-isoproyl, d-isobutyl, d-threo-isopropyl, d-threo, isopropyl, sec-butyl and t-butyl.

Alkyl phenidates, racemic mixtures and isolated individual isomers are known in the art, as disclosed in U.S. Pat. No. 2,507,631, issued May 16, 1950 to Hartmann et al, U.S. Pat. No. 2,157,880, issued Oct. 25, 1960 to Rometsch, and U.S. Pat. No. 5,908,850 issued Jun. 1, 1999 to Zeitlin et al; which references are incorporated herein in their entireties by reference thereto. Alkyl phenidates are commercially available, including by way of example, dextro-threo-methylphenidate (Focalin®) and isopropylphenidate.

Without wishing to be bound by any theory or mechanism, it is believed that the nonlinear lower alkyl phenidates provide hindrance to unwarranted esterfication which in turn causes adverse side effects, particularly adverse in children.

In the art related to the treatment of hyperactivity in children, particularly including ADD and ADHD, it is established practice to administer methylphenidate. Psychosocial behavioral disorders such as lack of attentiveness and verbal regression are improved with the administration of methylphenidate, as disclosed in U.S. Pat. No. 6,121,261, issued Sep. 19, 2006 to Glatt et al; and Creager et al., Journal of Speech and Hearing Research, 623-628 (1967). Methylphenidate is administered daily to children suffering psychobehavioral and neuropsychological disorders. The behavioral improvement is short lived, and lasts, at most, several hours after administration of the methylphenidate. Unless such daily dosages are maintained, the subject reverts to his or her attention deficits and hyperactivity.

One further most preferred methylphenidate is an extended release powder in aqueous suspension as disclosed in US 2013/0004571A1, published Jan. 3, 2013 to Metha et al., which is incorporated herein in its entirety by reference thereto. The aqueous suspension is particularly administrable to children with infantile cerebral palsy.

The foregoing Examples demonstrate that diseases or disorders, particularly including cerebral palsy and Rett syndrome having secondary speech and limits impairments are treated by the present invention.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the subject being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A pharmaceutical intervention for a gait or limb impairment and speech impairment secondary to a genetically or in utero acquired neurogenic disease or disorder, in a subject in need of the intervention, wherein said pharmaceutical intervention comprises:
   a psychostimulant having mood-elevating or anti-depressant activity affecting neural pathways effecting gait or limb and speech;
   whereby the gait or limb and speech impairments are diminished.

2. The pharmaceutical intervention of claim 1, wherein the psychostimulant comprises a methylphenidate.

3. The pharmaceutical intervention of claim 2, wherein the methylphenidate comprises dextro-threo-methylphenidate.

4. The pharmaceutical intervention of claim 2, wherein the methylphenidate comprises an analog of methylphenidate.

5. The pharmaceutical intervention of claim 1, said psychostimulant comprises a non linear lower alkyl phenidate.

6. The pharmaceutical intervention of claim 1, wherein the speech impairment comprises dysarthric speech.

7. The pharmaceutical intervention of claim 1, wherein the gait impairment comprises toe-to-heel gait.

8. The pharmaceutical intervention of claim 7, wherein the heel-to-toe gait is greater than toe-to-heel gait after the pharmaceutical intervention.

9. The pharmaceutical intervention of claim 8, wherein the improved heel-to-toe gait persists when the pharmaceutical intervention is no longer efficaciously present.

10. The pharmaceutical intervention of claim 1, wherein the disorder comprises cerebral palsy.

11. The pharmaceutical intervention of claim 1, wherein the gait impairment comprises spastic diplegia.

12. The pharmaceutical intervention of claim 1, wherein the psychostimulant comprises a norepinephrine-dopamine reuptake inhibitor (NDRI).

13. The pharmaceutical intervention of claim 1, wherein the impairment is first manifested when the subject is a child.

14. The pharmaceutical intervention of claim 13, wherein the psychostimulant comprises dextro-threo-methylphenidate.

15. A pharmaceutical intervention for a gait or limb impairment secondary to a genetically or in utero acquired neurogenic disease or disorder in a subject in need of such intervention, said intervention comprises a norepinephrine-dopamine reuptake inhibitor (NDRI), wherein the impairment is diminished, the disease or disorder persists, and the diminishment in the impairment persists when the NDRI is no longer efficaciously present.

16. The pharmaceutical intervention of claim 15, wherein the gait impairment comprises spastic diplegia.

17. The pharmaceutical intervention of claim 16, wherein spastic diplegia comprises toe-to-heel gait, and the heel-to-toe gait is greater than the toe-to-heel gait after the pharmaceutical intervention.

18. The pharmaceutical intervention of claim 17, wherein the greater heel-to-toe gait persists when the NDRI is no longer efficaciously present.

19. The pharmaceutical intervention of claim 15, wherein the disease or disorder comprises cerebral palsy.

20. The pharmaceutical intervention of claim 15, wherein the disease or disorder comprises Rett syndrome.

21. The pharmaceutical intervention of claim 15, wherein the subject is a child.

22. The pharmaceutical intervention of claim 15, wherein the NDRI comprises dextro-threo-methylphenidate.

23. The pharmaceutical intervention of claim 15, wherein the disease or disorder comprises Rett syndrome, and the impairment comprises a limb impairment comprising non-specific hand wringing.

* * * * *